United States Patent [19]

Miller, Jr.

[11] Patent Number: 5,368,605
[45] Date of Patent: Nov. 29, 1994

[54] LAPAROSCOPIC SURGICAL INSTRUMENT

[76] Inventor: Herman A. Miller, Jr., 1284 E. 450 North, Warsaw, Ind. 46580

[21] Appl. No.: 28,210

[22] Filed: Mar. 9, 1993

[51] Int. Cl.$^5$ .............................................. A61B 17/32
[52] U.S. Cl. ................................... 606/170; 606/174; 606/207
[58] Field of Search ................ 606/174, 170, 205–211, 606/127, 128; 128/751–755

[56] References Cited

U.S. PATENT DOCUMENTS

| | | | |
|---|---|---|---|
| 4,258,716 | 3/1981 | Sutherland | 606/174 |
| 4,433,687 | 2/1984 | Burke et al. | 606/174 |
| 4,760,848 | 8/1988 | Hasson | 606/174 |
| 4,994,079 | 2/1991 | Genese et al. | 606/206 |
| 5,184,625 | 2/1993 | Cottone, Jr. et al. | 128/751 |

Primary Examiner—Peter A. Aschenbrenner
Assistant Examiner—William W. Lewis
Attorney, Agent, or Firm—Lundy and Associates

[57] ABSTRACT

A tool for laparoscopic surgery comprising an elongated handle, an actuator connected to the handle between the opposite ends, a bore extending therethrough, a tool rod positioned in the bore, an actuator connected to the handle and engaging the tool rod for reciprocal motion within the bore. A sleeve extends over the tool rod and is secured to the handle. An instrument is secured to the tool rod at its distal end and is actuable by the sliding motion of the tool rod within the handle and sleeve. The handle has a cylindrical external surface and a grip remote from the distal end of the handle such that the handle can be held in the surgeon's hand like a writing instrument and the actuator be manipulated by the forefinger of the hand holding the tool to operate the instrument equally conveniently by right handed and left handed surgeons.

14 Claims, 3 Drawing Sheets

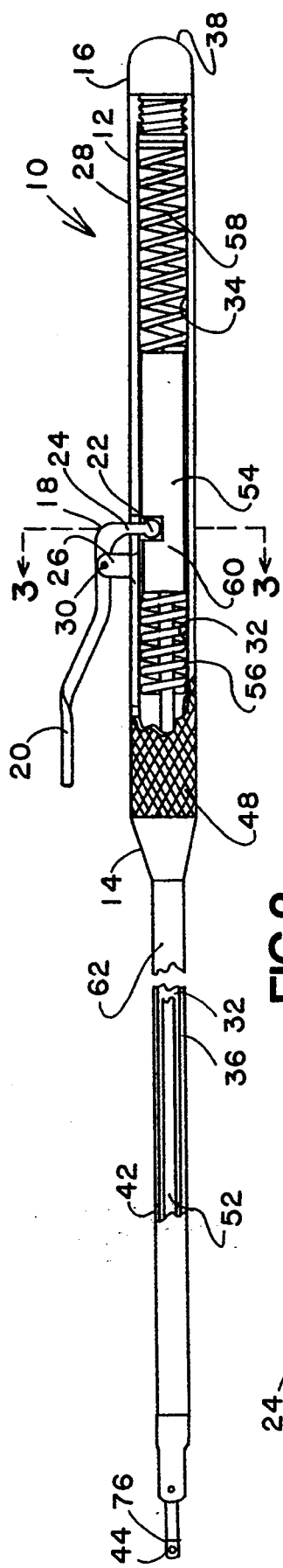
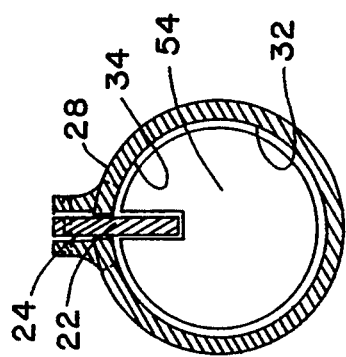
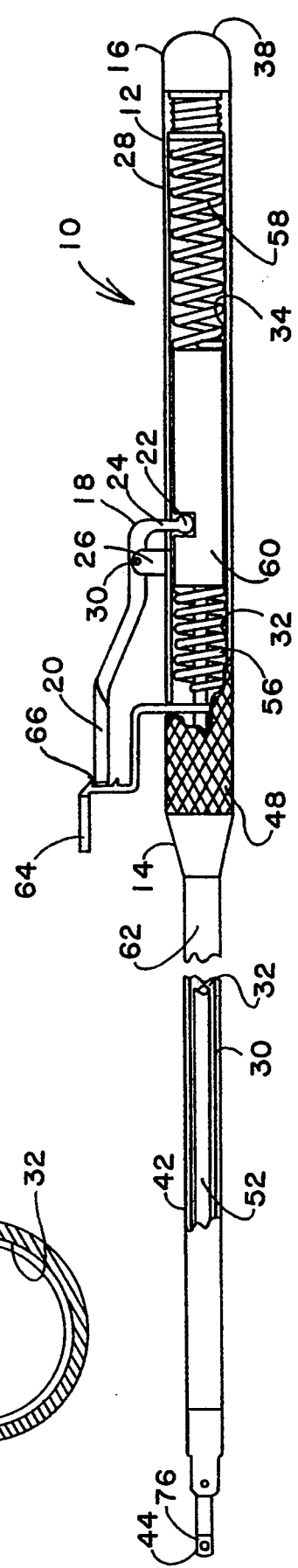
FIG.2
FIG.3
FIG.4

LAPAROSCOPIC SURGICAL INSTRUMENT

BACKGROUND OF THE INVENTION

The present invention pertains to surgical instruments, and more particularly pertains to those surgical instruments used in laparoscopic surgery.

There are many surgical instruments heretofore proposed. A great variety of those surgical instruments, such as saws, clamps, scissored cutters, forceps and the like, these same instruments are required for laparoscopic surgery. However, each of these instruments must be provided with the same functionality at the end of an elongated rod or shaft many times longer than the conventional instruments, e.g., 10 to 28 inches (25 to 75 centimeters).

The instrument must also be actuable by a handle at the end opposite the instrument. Heretofore, such instruments have bad handles and actuators on the handle which are unique to the instrument. Additionally, some of the handles and actuators are ergonomically designed for right handers but are clumsy and not convenient to use by left handers. Since laparoscopic surgery requires precision and accuracy throughout the surgical procedure, any clumsiness of the instrument or any feature which renders the instrument not convenient to use is not desirable.

It is therefore highly desirable to provide improved instruments for laparoscopic surgery.

It is also highly desirable to provide an improved family of instruments for laparoscopic surgery which are actuable by like handles such that each instrument of the family has the same feel to the surgeon.

It is also highly desirable to provide an instrument for laparoscopic surgery which has an improved actuator and an improved handle.

It is also highly desirable to provide an improved family of instruments for laparoscopic surgery each of which has like handles and like actuators such that each instrument of the family has the same feel to the surgeon.

It is also highly desirable to provide an improved instrument for laparoscopic surgery which can be equally conveniently used by both right handed surgeons and left handed surgeons.

It is also highly desirable to provide an improved instrument for laparoscopic surgery which is relatively inexpensive to manufacture, can be easily cleaned, disinfected and autoclaved, if necessary.

It is finally highly desirable to provide an improved instrument for laparoscopic surgery having all of the above desired features.

SUMMARY OF THE INVENTION

It is therefore an object of the invention to provide improved instruments for laparoscopic surgery.

It is also an object of the invention to provide an improved family of instruments for laparoscopic surgery which are actuable by like handles such that each instrument of the family has the same feel to the surgeon.

It is also an object of the invention to provide an instrument for laparoscopic surgery which has an improved actuator and an improved handle.

It is also an object of the invention to provide an improved family of instruments for laparoscopic surgery each of which has like handles and like actuators such that each instrument of the family has the same feel to the surgeon.

It is also an object of the invention to provide an improved instrument for laparoscopic surgery which can be equally conveniently used by both right handed surgeons and left handed surgeons.

It is also an object of the invention to provide an improved instrument for laparoscopic surgery which is relatively inexpensive to manufacture, can be easily cleaned, disinfected and autoclaved, if necessary.

It is finally an object of the invention to provide an improved instrument for laparoscopic surgery having all of the above desired features.

In the broader aspects of the invention, there is provided a tool for laparoscopic surgery comprising an elongated handle, an actuator connected to the handle between the opposite ends, a bore extending therethrough, a tool rod positioned in the bore, an actuator connected to the handle and engaging the tool rod for reciprocal motion within the bore. A sleeve extends over the tool rod and is secured to the handle. An instrument is secured to the tool rod at its distal end and is actuable by the sliding motion of the tool rod within the handle and sleeve. The handle has a cylindrical external surface and a grip remote from the distal end of the handle such that the handle can be held in the surgeon's hand like a writing instrument and the actuator be manipulated by the forefinger of the hand holding the tool to operate the instrument equally conveniently by right handed and left handed surgeons.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 2 is a sectional, view taken along section line 2—2 of FIG. 1.

FIG. 3 is a cross-sectional view taken essentially along section line 3—3 of FIG. 1.

FIG. 4 is a sectional view like FIG. 2 of the improved laparoscopic surgical instrument of the invention with a locking lever.

DESCRIPTION OF A SPECIFIC EMBODIMENT

Figure 1:
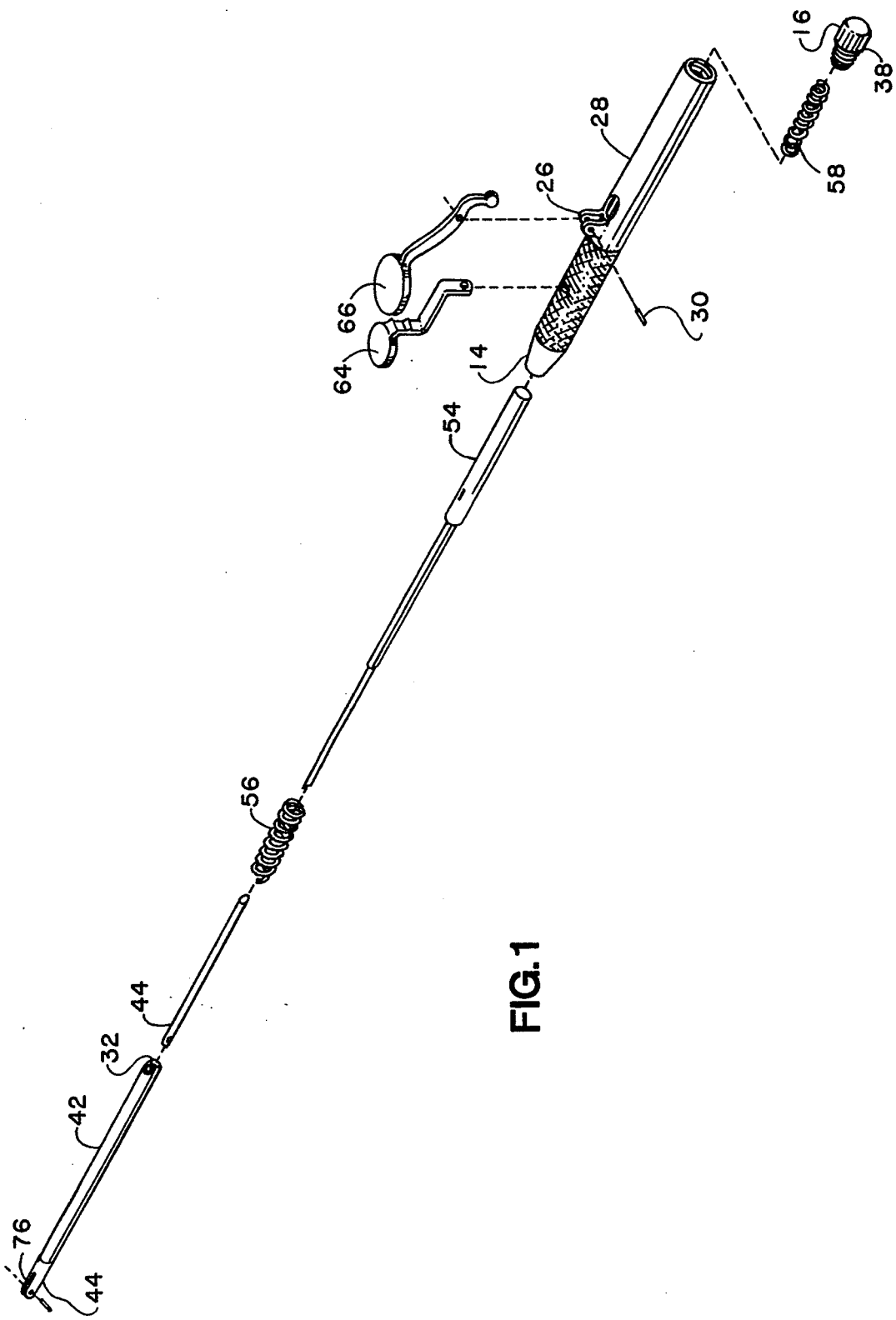
FIG. 1 is an exploded view of the improved laparoscopic surgical instrument of the invention.

Referring to FIGS. 1—3, a tool 10 for laparoscopic surgery is shown having an elongated handle 12 with a forward end 14 and a rearward end 16. An actuator 18 is connected to the handle 12 between the opposite ends 14, 16. The actuator 18 has an exterior portion 20 which extends over the handle 12 and an interior portion 22 which extends through an opening 24 (to be mentioned hereinafter). The actuator 18 is supported on the handle 12 by a pair of ears 26 which are secured to the exterior surface 28 of the handle 12 between which the actuator 18 is positioned and a pivot rod 30 extending through the ears 26 and the actuator 18.

The handle 12 has a generally cylindrical exterior surface 28 and a generally cylindrical bore 32 extending therethrough. Bore 32 has a larger diameter bore 34 adjacent the rearward end 16 and a smaller diameter bore 36 adjacent the forward end 14. The bore 32 is threaded at the rearward end 16 and an end cap 38 is threadedly secured in the bore 32 at the rearward end 16.

A step 40 is positioned between the larger diameter bore 34 and the smaller diameter bore 36. The step 40 faces the rearward end 16.

A tubular sleeve 42 is positioned within the smaller bore 36 and extends outwardly of the handle 12. The sleeve 42 has a distal end 44 to which the tool 46 is attached as will be explained hereinafter. Handle 12 has a grip 48 on its exterior surface 28 between the forward end 50 of the handle 12 and the actuator 18. Exterior portion 20 of actuator 18 extends over grip 48.

A tool rod 52 is positioned within the step diameter bore 32 of tie handle 12 and the sleeve 42. Tool rod 52 has an enlarged portion 54 that is positioned within the larger bore 34. A spring 56 is positioned around the tool rod 52 between the larger portion 54 and the step 40. A second spring 58 is positioned in larger bore 34 between the enlarged portion 54 of the tool rod 52 and the end cap 38.

The tool rod 52 is positioned within the handle 12 and the sleeve 42 and biased in both directions for reciprocal motion therein. Enlarged portion 54 has an opening 60 therein in which interior portion 22 of actuator 18 is positioned. The interior portion 22 of actuator 18 in said opening 60 extends through opening 24 in handle 12. The interior portion 22 of the actuator pivots with regard to the enlarged portion 54 of the tool rod 52 in opening 60 as the actuator 18 is moved. Motion of the actuator 18 about pivot rod 30 causes the tool rod 52 to reciprocate the bore 32 against the bias of the springs 56, 58.

A lubricating sleeve 62 is positioned around tube tool rod 52 adjacent its enlarged portion 54. This lubricating sleeve 62 extends within the sleeve 42. The lubricating sleeve 62 may move with tool rod 52 or be stationary with the sleeve 42. In either event, the lubricating sleeve 62 spaces the tool rod 52 from the interior walls of the bore 32 and allows the tool rod 52 to reciprocate within the bore 32 and the sleeve 42 with minimum of friction. In a specific embodiment, the lubricating sleeve 62 is made of polyethylene or some other self-lubricating material.

In a specific embodiment, the grip 48 extends axially of the handle 12 for about 10% to about 30% of the actual length of the handle 12. The grip 48 is positioned remotely of the rearward end 16 of the handle 12. In other specific embodiments, the sleeve 42 extends frown the handle 12 greater than 2 times the length of the handle 12.

Referring to FIG. 4, a laparoscopical surgical instrument 10 as shown in FIG. 1 is shown with a locking lever 64. Locking lever 64 is secured to handle 12 beneath the actuator 18 adjacent to the grip 48 of the handle 12. The locking lever 64 engages the actuator 18 at several positions .and locks the actuator 18 in a desired position. Locking lever 64 is resiliently movable toward and away from the grip 48 by pressing downwardly toward the handle 12 the most distal portion 66. The resiliency of the locking lever 64 places the locking lever 64 in position to engage the actuator 18 whenever the actuator 18 is moved into contact with the locking lever 64. In all other aspects, the laparoscopic surgical instrument 10 shown in FIG. 4 is identical to that shown in FIGS. 1–3.

Figure 6:
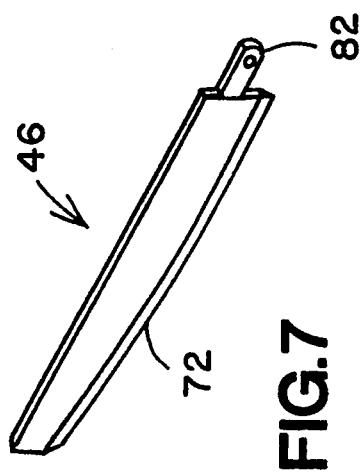
FIG. 6 is a perspective view of the pliers/wrench implement of the invention.
Figure 7:
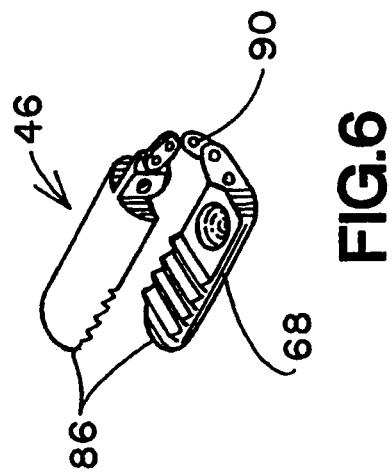
FIG. 7 is a perspective view of the knife implement of the invention.
Figure 5:
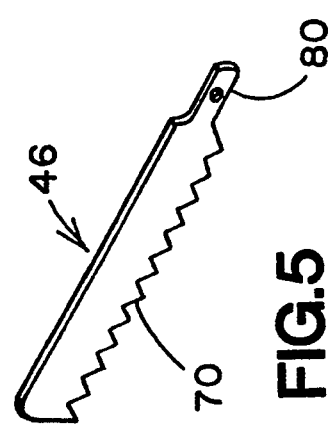
FIG. 5 is a perspective view of the saw implement of the invention.

FIGS. 5–8 illustrate various tools which can be secured to the distal end 44 of the sleeve 42. These tools range from pliers or wrench 68 as shown in FIG. 6, to a saw 70 shown in FIG. 5, to a knife blade 72 shown in FIG. 7, and to scissors 74 shown in FIG. 8. Both the saw 70 and the knife blade 72 of FIGS. 5 and 7 are inserted between two ears 76 of sleeve 42 for sliding motion. At one end 80 of the saw 70 shown in FIG. 5 and the knife blade 72 shown in FIG. 7 are secured to the tool rod 52 such that the saw and knife blade reciprocate with the tool rod 52.

Figure 8:
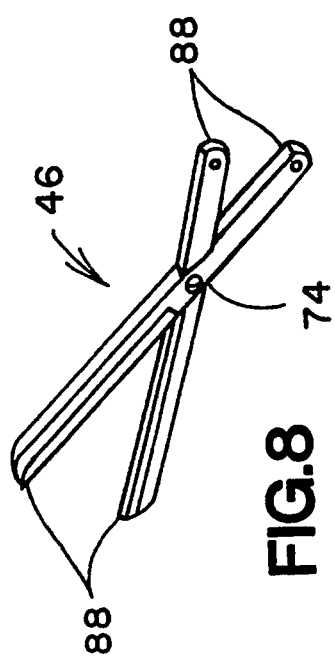
FIG. 8 is a perspective view of the scissors implement of the invention.

Both the scissors 74 and the pliers or wrench 68 of FIGS. 6 and 8 are connected by pivots 88 and 90 to the opposite ears 76 of the sleeve 42, and at the same time, connected to the tool rod 52. The reciprocation of the tool rod 52 as above described opens and closes the jaws 84 of the pliers or wrench 68, and the blades 86 of the scissors 74. The positioning of the respective pivots 88, 90 and the connection to the tool rod 52 and the connection between the actuator 18 and the tool rod 52 are positioned such that when the actuator 18 is depressed and locked by locking lever 64, the pliers 68 are closed and the scissors 74 are closed.

In specific embodiments, scissors 74, pliers 68, saw 70, and knife blade 72 are made of surgical steel. Tool rod 52, locking lever 64 and the actuator 18 are each made of surgical steel. The springs 56 and 58 are made of spring stainless steel. The handle 12 and sleeve 42 are made of thermosetting plastic capable of being autoclaved. In a specific embodiment, the handle 12 measures from about 3.5 to 5 inches and is approximately $\frac{3}{8}$ inches in diameter.

In the specific embodiment illustrated, handle 12 is about 5 inches long and about $\frac{3}{8}$ inches in diameter. Grip 48 is about 1-$\frac{1}{2}$ inches long and is positioned about 3 inches from rearward end 16. Pivot 30 of ears 26 is positioned about 2-$\frac{3}{4}$ inches from end 16 and tool rod 52 and sleeve 62 extend from handle 12 from about 5 to about 24 inches thereby making the total length of the surgical instrument 10 from about 10 to about 28 inches. The surgical "feel" of the instrument 10 is determined by the choice of springs 56 and 58. In a specific embodiment, spring 56 is a stainless steel spring having a spring OD of about 0.120 inches, a wire OD of about .0018 inches, a spring constant of about 5-$\frac{1}{2}$ pounds per inch, and a length of about $\frac{3}{4}$ inch. In the same embodiment, spring 58 has a spring OD of about 0.24 inches, a wire OD of about 0.0032 inches, spring constant of about 16 pounds per inch, and a length of about 1 inch.

In operation, the improved laparoscopic surgical instrument 10 of the invention can be used with one or more of the tools 68, 70, 72 and 74 affixed to the distal end 44 of sleeve 42 and operated by manipulation of the actuator 18 by surgeons relatively skillfully. The surgical technique dictates the length of the sleeve 42. In all embodiments, the length and diametral size of the handle 12 remains the same. The handle 12 is designed such that it can be held by the surgeon in the same manner as a writing instrument and the actuator 18 can be manipulated by the forefinger of the hand holding the laparoscopic surgical instrument 10.

By the forefinger depressing the actuator 18, the tool rod 52 reciprocates against the resiliency of the springs 56 and 58 and opens and closes the scissors 74 in a cutting action, opens and closes the pliers or wrench 68, reciprocates the saw 70 or the knife blade 72 as desired. In the embodiment including the locking lever 64, the pliers 68 can be locked shut by the locking lever 64 and function as a locking wrench.

The improved laparoscopic surgical instrument 10 of the invention provides a family of improved instruments for laparoscopic surgery having a like handle by which all of the instruments of the family are actuable in the same way. Thus, the family of surgical instruments 10 each will have the same feel to the surgeon. The improved instrument 10 for laparoscopic surgery of the invention has an improved actuator 18 and an improved handle 12 which allows the surgical tool to be actuated more conveniently by both right-handed and left-handed surgeons. The improved laparoscopic surgical instrument 10 of the invention is relatively inexpensive to manufacture, can be completely disassembled, disinfected, and autoclaved if necessary to maintain surgical cleanliness standards.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A tool for laparoscopic surgery comprising an elongated handle having a forward end and a rearward end, said handle having an identical exterior shape for both right handed persons and left handed persons, an actuator connected to said handle between said ends, said handle having a bore extending therethrough, said handle having a grip between said actuator and said forward end, said actuator extending over said grip, a tool rod positioned in said bore for reciprocation therein, an implement connected to said forward handle end for actuation, said tool rod connected to said tool whereby said tool is actuated upon reciprocation of said tool rod in said bore, said actuator being connected to said tool rod, said actuator being movable with said reciprocation of said tool rod, said bore being generally cylindrical and having a larger diameter bore adjacent to said rearward end and a smaller diameter bore adjacent said forward end with a step therebetween, said tool rod having an enlarged portion in said larger diameter bore, a spring positioned in said handle between said step and said enlarged portion, a second spring positioned within said handle between said enlarged portion and said rearward end of said handle, whereby said handle can be held like a writing instrument and the actuator may be manipulated by the forefinger of the hand holding said tool to actuate said tool.

2. The tool of claim 1 wherein said handle comprises a larger portion adjacent said rearward end and a sleeve, said sleeve extends over said tool rod and is secured to said larger portion, said tool is connected to the distal end of said sleeve for actuation.

3. The tool of claim 1 wherein said tool rod is biased toward an extended position, said actuator being movable from an at rest position toward said handle, said actuator motion toward said handle corresponding to reciprocation of said tool rod toward said rearward end.

4. The tool of claim 3 wherein said implement is chosen from the group of implements consisting of scissors, saws, knives, and pliers.

5. The tool of claim 1 wherein said implement is chosen from the group of implements consisting of scissors, saws, knives, and pliers.

6. The tool of claim 1 wherein said tool rod is biased toward an extended position, said actuator being movable from an at rest position toward said handle, said actuator motion toward said handle corresponding to reciprocation of said tool rod toward said rearward end.

7. The tool of claim 6 further comprising a lock, said lock engaging said actuator in an actuated position, said actuator in its locked position holding said tool rod against the urging of said spring.

8. The tool of claim 6 wherein said handle has a cylindrical exterior surface, said sleeve is greater than two times the length of said larger handle portion, said grip is on said larger portion and extends from about 10% to about 30% of the actual length of said larger portion, said grip being remote from said rearward end of said handle.

9. The tool of claim 8 wherein said implement is chosen from the group of implements consisting of scissors, saws, knives, and pliers.

10. A tool for laparoscopic surgery comprising an elongated handle having a forward end and a rearward end, said handle having an identical exterior shape for both right handed persons and left handed persons, an actuator connected to said handle between said ends, said handle having a bore extending therethrough, said handle having a grip between said actuator and said forward end, said actuator extending over said grip, a tool rod positioned in said bore for reciprocation therein, an implement connected to said forward handle end for actuation, said tool rod connected to said tool whereby said tool is actuated upon reciprocation of said tool rod in said bore, said actuator being connected to said tool rod, said actuator being movable with said reciprocation of said tool rod, whereby said handle can be held like a writing instrument and the actuator may be manipulated by the forefinger of the hand holding said tool to actuate said tool, said handle comprising a larger portion adjacent said rearward end and a sleeve, said sleeve extending over said tool rod and is secured to said larger portion, said tool being connected to the distal end of said sleeve for actuation, said sleeve being greater than two times the length of said larger handle portion.

11. A tool for laparoscopic surgery comprising an elongated handle having a forward end and a rearward end, said handle having an identical exterior shape for both right handed persons and left handed persons, an actuator connected to said handle between said ends, said handle having a bore extending therethrough, said handle having a grip between said actuator and said forward end, said actuator extending over said grip, a tool rod positioned in said bore for reciprocation therein, an implement connected to said forward handle end for actuation, said tool rod connected to said tool whereby said tool is actuated upon reciprocation of said tool rod in said bore, said actuator being connected to said tool rod, said actuator being movable with said reciprocation of said tool rod, whereby said handle can be held like a writing instrument and the actuator may be manipulated by the forefinger of the hand holding said tool to actuate said tool, said handle comprising a larger portion adjacent said rearward end and a sleeve, said sleeve extending over said tool rod and being secured to said larger portion, said tool being connected to the distal end of said sleeve for actuation, said grip being on said larger portion and extends from about 10% to about 30% of the actual length of said larger portion, said grip being remote from said rearward end of said handle.

12. A tool for laparoscopic surgery comprising an elongated handle having a forward end and a rearward end, said handle having an identical exterior shape for both right handed persons and left handed persons, an actuator connected to said handle between said ends, said handle having a bore extending therethrough, said handle having a grip between said actuator and said forward end, said actuator extending over said grip, a tool rod positioned in said bore for reciprocation therein, an implement connected to said forward handle end for actuation, said tool rod connected to said tool whereby said tool is actuated upon reciprocation of said tool rod in said bore, said actuator being connected to said tool rod, said actuator being movable with said reciprocation of said tool rod, whereby said handle can be held like a writing instrument and the actuator may be manipulated by the forefinger of the hand holding said tool to actuate said tool, said handle comprising a larger portion adjacent said rearward end and a sleeve, said sleeve extending over said tool rod and being secured to said larger portion, said tool being connected to the distal end of said sleeve for actuation, said sleeve having an axial length at least two times that of said larger diameter portion of said handle.

13. A tool for laparoscopic surgery comprising an elongated handle having a forward end and a rearward end, said handle having an identical exterior shape for both right handed persons and left handed persons, an actuator connected to said handle between said ends, said handle having a bore extending therethrough, said handle having a grip between said actuator and said forward end, said actuator extending over said grip, a tool rod positioned in said bore for reciprocation therein, an implement connected to said forward handle end for actuation, said tool rod connected to said tool whereby said tool is actuated upon reciprocation of said tool rod in said bore, said actuator being connected to said tool rod, said actuator being movable with said reciprocation of said tool rod, a spring being positioned within said bore between said handle and said tool rod, whereby said reciprocating motion of said tool rod causes said spring to expand and contract, a tube of lubricating material is positioned between said sleeve and said tool rod, whereby said handle can be held like a writing instrument and the actuator may be manipulated by the forefinger of the hand holding said tool to actuate said tool.

14. A tool for laparoscopic surgery comprising an elongated handle having a forward end and a rearward end, said handle having an identical exterior shape for both right handed persons and left handed persons, an actuator connected to said handle between said ends, said handle having a bore extending therethrough, said handle having a grip between said actuator and said forward end, said actuator extending over said grip, a tool rod positioned in said bore for reciprocation therein, an implement connected to said forward handle end for actuation, said tool rod connected to said tool whereby said tool is actuated upon reciprocation of said tool rod in said bore, said actuator being connected to said tool rod, said actuator being movable with said reciprocation of said tool rod, a lock, said lock engaging said actuator in an actuated position, said actuator in its locked position holding said tool rod against the urging of said spring, whereby said handle can be held like a writing instrument and the actuator may be manipulated by the finger of the hand holding said tool to actuate said tool.

* * * * *